United States Patent [19]

Fischer et al.

[11] Patent Number: 5,383,453
[45] Date of Patent: Jan. 24, 1995

[54] METHOD FOR MANUFACTURING AN OPTICAL PROBE

[75] Inventors: Bernhard Fischer, Leonberg; Martin Wunderling, Boeblingen; Martin Guenther, Wildberg, all of Germany

[73] Assignee: Hewlett-Packard Company, Palo Alto, Calif.

[21] Appl. No.: 749,697

[22] Filed: Aug. 26, 1991

[30] Foreign Application Priority Data

Sep. 17, 1990 [EP] European Pat. Off. ............ 90117845

[51] Int. Cl.⁶ .............................................. A61B 5/00
[52] U.S. Cl. ...................................... 128/634; 29/428; 29/517
[58] Field of Search ..................... 29/428, 517; 128/634

[56] References Cited

U.S. PATENT DOCUMENTS 4,005,522  2/1977  Dalgleish ............................... 29/517
4,220,398  9/1980  Dalgoutte ........................ 350/96.21

FOREIGN PATENT DOCUMENTS 0159198  12/1985  European Pat. Off. .
0279004   8/1988  European Pat. Off. .
0336984  10/1989  European Pat. Off. .
0336985  10/1989  European Pat. Off. .

OTHER PUBLICATIONS

S. R. Goldstein et al., "A Miniature Fiber Optic pH Sensor for Physiological Use", *Journal of Biomechanical Engineering*, May 1980, vol. 102, pp. 141–146.

J. L. Gehrich et al., "Optical Fluorescence and Its Application to an Intravascular Blood Gas Monitoring System", *IEEE Transactions on Biomedical Engineering*, Feb. 1986, No. 2, pp. 117–132.

*Primary Examiner*—Randall L. Green
*Assistant Examiner*—Rob Clarke

[57] ABSTRACT

An improved optical probe for the invasive measurement of blood parameters is disclosed that minimizes reading inaccuracy due to mechanical stresses. An optical probe for the invasive measurement of blood parameters is typically made up of various sensors that end in a sheath. Each sensor is connected to a monitor via an optical fiber. The optical fibers are surrounded by a tube. In the region where the sheath adjoins the tube, the sheath is deformed by crimping such that a better mechanical contact (form-locking) between the sheath, the sensors, and the tube can be obtained, in order to avoid systemic errors caused by displacement of the optical fibers inside the sheath.

12 Claims, 5 Drawing Sheets

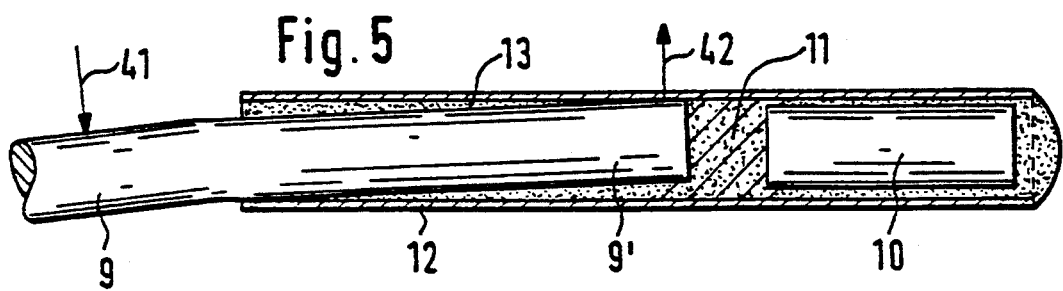
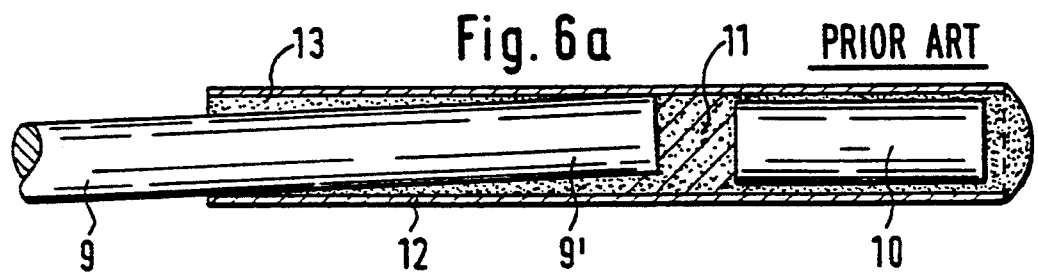
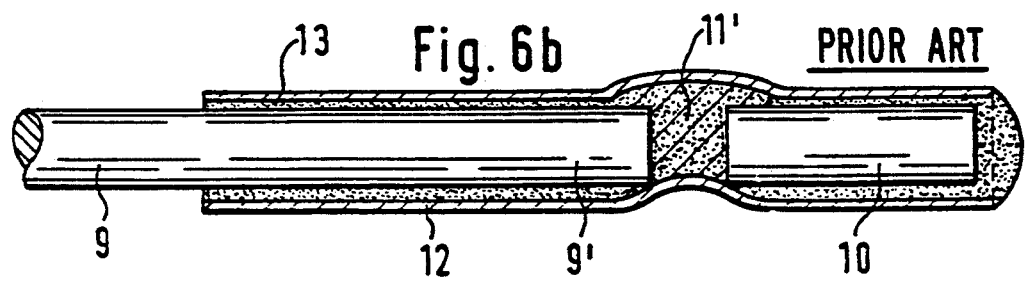
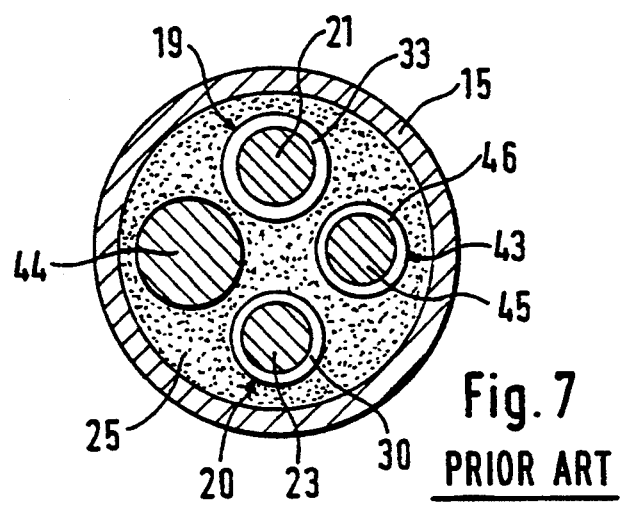

METHOD FOR MANUFACTURING AN OPTICAL PROBE

BACKGROUND OF THE INVENTION

The present invention relates to an optical probe for the invasive measurement of blood parameters in a biologic circulatory system.

Probes for the invasive measurement of blood parameters usually consist of at least one sensor that is connected with an associated monitor via an optical fiber. Typically, such probes comprise between 1 and 3 sensors, e.g., intended for the measurement of blood gases such as partial oxygen pressure ($pO_2$) or partial carbon dioxide pressure ($pCO_2$), or for the measurement of the pH value of the blood. All these sensors have a similar mechanical construction. The optical fiber in each sensor ends with a gel containing a dye. The optical density or another optical parameter of the dye varies with the blood parameter to be measured. Light emitted by the associated monitor and transmitted via the optical fiber is fed into the gel and passes through it. The light is then fed back via the same or another optical fiber to the monitor, which contains a detector to measure light attenuation or changes in other optical parameters caused by the dye. This attenuation or change is a function of the blood parameter to be measured, and the relationship between attenuation, absorbance, or the change of another optical parameter and the blood parameter is well-known.

Usually, a reflector is positioned adjacent to the dye-containing gel, opposite to the optical fiber. In such a sensor, light transmitted through the optical fiber passes the gel, is reflected at the reflector, passes the gel again and is then transmitted back. In this environment, only one optical fiber is required for each sensor. Further, as the light passes the dye-containing gel twice, it is easier to detect any change in the optical characteristics of that dye. However, there are also other alternatives such as directing the light to a second optical fiber (when it has passed the gel) and feeding the second optical fiber back to the monitor. The key point in all of these cases is that the light has to pass the gel zone where its optical characteristics are altered.

The end of the fiber, the gel, and the reflector are surrounded by a semi-permeable or selective membrane (for example, a hydrogen ion permeable envelope in the case of a pH sensor). This membrane permits, on the one hand, only selected ions or molecules to reach the dye-containing gel; on the other hand, it has a mechanical function, namely to keep the gel in place.

In this description, and as it is usual in the art, the region of the dye-containing gel, together with the part of the membrane in this region, is called the "diffusion zone."

Optical probes as described herein usually comprise three or more sensors in order to measure various blood parameters with one probe. In these cases, the single optical fibers associated with the respective sensors are combined in a single cable for connection with the associated monitor. However, it is also possible to build an optical probe with one or two sensors only. Optical probes can be introduced into a patient's artery to measure—depending on the dye—various blood parameters such as pH, $pO_2$ or $pCO_2$, as described above. It is also possible to integrate further components such as a strain-relieving wire, an arterial pressure sensor, a temperature sensor, or the like into the probe. All of these components, including the sensors described above, will be referred to generically herein as sensing means.

Turning now in detail to the drawings, where like numerals designate similar elements, FIG. 1 depicts a typical system of the prior art for the invasive measurement of blood parameters, for example of the partial carbon dioxide pressure ($pCO_2$) or the pH value. The light of an optical transmitter 1 is directed into an optical fiber 2 (see arrow 2a). Preferably, this optical fiber 2 is a glass fiber. Usually a train of light pulses is used, but this is not a strict requirement. The light passes an optical coupler 3 and reaches tip 4 of the sensor, the tip being intended for introduction into the artery of a patient. Tip 4 of the sensor contains a gel into which a dye such as phenol red is immobilized. The dye modifies at least one optical parameter, preferably the intensity, of the light in an amount dependant on the $pCO_2$ (or, in other cases, the $pO_2$ or the pH) value of the blood. The modified light is reflected into the same fiber 2 and, after passing through optical coupler 3, reaches an optical receiver 5 (see arrow 5a). It is understood that optical transmitter 1 and optical receiver 5 are incorporated in a monitor or other measuring instrument 8. Dashed line 6 indicates a releasable connection between the probe 7 and the monitor 8. Thus the optical probe consists of a multiplicity of sensors and the related number of optical fibers; preferably, it comprises 3 sensors responsive to $pO_2$, $pCO_2$ and pH, respectively.

The operation of a single sensor will now be explained by means of FIG. 2, which shows a longitudinal section through a pH sensor. The mechanical construction of the pH sensor is typical for sensors of this type; the $pO_2$ and the $pCO_2$ sensor would have a similar construction. As shown in FIG. 2, the pH sensor comprises a glass fiber 9 and an optical reflector 10. Optical reflector 10 is made of stainless steel. Between the optical fiber 9 and the reflector 10, a gel 11 is located. This gel is used to immobilize a dye such as phenol red, the optical characteristics of which vary with the blood parameter—in this case, pH—to be measured. The surface 10a of the optical reflector 10 facing the gel 11 is polished.

The sensor is surrounded by a semi-permeable or selective membrane 12 that is fastened on the sensor by means of a glue 13. As FIG. 2 depicts, the glue is only introduced at the distal end of the sensor (left side in FIG. 2) and at the very proximal end. The selective membrane 12 is permeable to the ions or gas molecules to be measured. In case of the pH sensor shown in FIG. 2, the selective membrane 12 is permeable to $H^+$ ions.

FIG. 3 depicts a longitudinal section of the probe tip 14 of an optical probe comprising three sensors. A sheath 15 is closed at its outer end (proximal end) with a metal cap 16 and is connected, as shown by 17, with a tubing element 18. The connection between sheath 15 and tubing element 18 is secured by adhesive means. Tubing element 18 ends at a connector for connection to an appropriate monitor (not shown).

Sheath 15 contains three sensors, two of which are shown in FIG. 3, namely a pH sensor 19 and a $pCO_2$ sensor 20. A third sensor, namely a $pO_2$ sensor, is not shown in FIG. 3 as it is hidden behind $pCO_2$ sensor 20.

Each of the sensors is connected with the associated monitor via an optical fiber, as shown by optical fiber 21 (which is surrounded by an appropriate envelope 22) for the case of pH sensor 19 and optical fiber 23 for the $pCO_2$ sensor 20 (surrounded by envelope 24). The various sensors are fastened within sheath 15 by means of a silicone glue or adhesive 25.

Sheath 15 further comprises three openings, the first of which is labeled as 26 in FIG. 3, whereas the second opening 27 is hidden behind the $pCO_2$ sensor 20. The third opening is not shown in FIG. 3; it is contained in the broken-away part. These openings ensure that, when the probe tip is introduced into a patient's artery, the sensors are in contact with the blood, thus allowing gas molecules and hydrogen ions to reach the sensors.

$PCO_2$ sensor 20 further comprises a dye-containing gel 28 and an optical reflector 29. The region where dye-containing gel 28 is located is also called the "diffusion zone." Sensor 20 is, insofar as contained in sheath 15, surrounded by a semi-permeable membrane 30 that is fixed on optical fiber 23 and reflector 29 by means of a further glue or adhesive.

In similar manner, pH sensor 19 comprises a dye-containing gel 31, a reflector 32, and a semi-permeable membrane 33.

It is understood that the probe depicted in FIG. 3 is only one example of an invasive optical blood parameter probe. In other embodiments, the probe can comprise only one or two sensors, or even more elements, such as a strain relieving wire, all generically referred to as sensing means.

For a more detailed description of invasive fiber optic blood parameter measurement, reference is made to "Optical Fluorescence and its Application to an Intravascular Blood Gas Monitoring System," IEEE Transactions on Biomedical Engineering, Vol. BME-33, No. 2, February 1986, pages 117 et seq., and "A Miniature Fiber Optic pH Sensor for Physiological Use," Journal of Biomedical Engineering, May 1980, pages 141 et seq. Examples of the construction of an optical probe incorporating multiple sensors are described in European Patent Applications 279 004, 336 984, and 336 985, which are incorporated into the disclosure of this description by reference.

The latter European Patent Applications also describe a further advantageous component of the optical probe. This component is a sheath, usually a metal sheath, covering the proximal end of the sensors that keeps them together mechanically. The sheath is connected to a tubing element that covers the optical fibers (preferably, the tube is introduced into the sheath). Whether the sheath encloses a portion of the tube or the sheath and tube merely abut, they can be described as being in contact with each other.

Extensive tests have shown that the stability of the sensor readings in these types of optical probes is not always satisfactory. In particular, it has turned out that the sensor readings, once the sensors were used—either in a natural or an artificial blood vessel—differed from the readings of an unused sensor. By way of example, a probe was exposed to a certain chemical environment, but no mechanical stress, and its readings ($pO_2$, $pCO_2$ and pH) were recorded. Then, the same probe was exposed to mechanical stress, like the introduction into a natural or artificial blood vessel and subsequent withdrawal, and its readings were again recorded. In many cases, the second readings differed significantly from the first readings. This difference in the readings seemed to be a systemic error. Furthermore, the observed deviation did not disappear when the mechanical stress ended, i.e., the accuracy of the probe was permanently impaired.

This error affects the accuracy of the probe. Even worse, the error cannot be fully compensated for by recalibration of the sensor(s). Sensors of the type described herein are calibrated immediately before use. After introduction into a blood vessel, only a 1-point calibration (e.g., by comparison with the parameter value of the blood obtained by other methods such as in vitro blood sample analysis) can be done. Such a 1-point calibration can compensate for the constant offset, but it cannot compensate for a change in sensitivity caused by mechanical stress. In other words, neither a second point defining the slope of the sensor's characteristic curve, nor the slope itself, can be recalibrated.

Accordingly, there exists a need for an improved optical probe of the kind described above that avoids, minimizes, or reduces the reading errors occuring after the probe is subjected to mechanical stress.

SUMMARY OF THE INVENTION

It is an objective of the present invention to provide an optical probe with one or more blood parameter sensors that avoids, minimizes, or reduces the reading errors occurring after the probe is subjected to mechanical stress. In accordance with this invention, a sheath surrounding the sensors and an optically sensitive dye-containing gel is deformed with respect to its originally circular cross-sectional shape, at least in the region adjoining a tube covering the optical fibers used in the probe, such that the circumferential arcing angle of the sheath (the looping angle) in relation to at least one of the sensors is larger than in the case of circular cross-section.

If the optical fibers have a better mechanical fixing or contact to the sheath in the region where they enter the sheath, less movement of the portions of the optical fibers extending into the sheath occurs. By means of the increased looping angle of circumference of the sheath, the respective optical fiber is in better mechanical contact to the sheath, which in turn prevents it from moving inside the sheath.

Crimping the region of the sheath adjoining the tube is even sufficient to avoid or restrict movement of the proximal end of the optical fiber inside the sheath. It is not necessary to deform the sheath along its whole length or along the region covering the optical fibers.

In an alternate embodiment, the sheath is deformed with respect to its originally circular shape, at least in the region adjoining the tube, such that the area of the cross-section not occupied by the sensors is smaller than in the case of circular cross-section. This reduces the free-space sectional area, which in turn reduces the freedom of movement of the optical fibers, so that they are kept in their position relative to the dye-containing gel.

Other objects, aspects, and advantages of the invention will be apparent to those skilled in the art upon the reading of the specification and the appended claims.

BRIEF DESCRIPTION OF THE DRAWING

FIG. 5 depicts, in cross-section, the effect of the bending stress on a sensor of the prior art.

FIGS. 6a and 6b depict two deformation effects when the bending stress has ended on the prior art sensor as shown in FIG. 5.

FIG. 7 is a cross-section through a prior art optical probe along line A—A of FIG. 3.

DETAILED DESCRIPTION OF PREFERRED EMBODIMENTS

Figure 1:
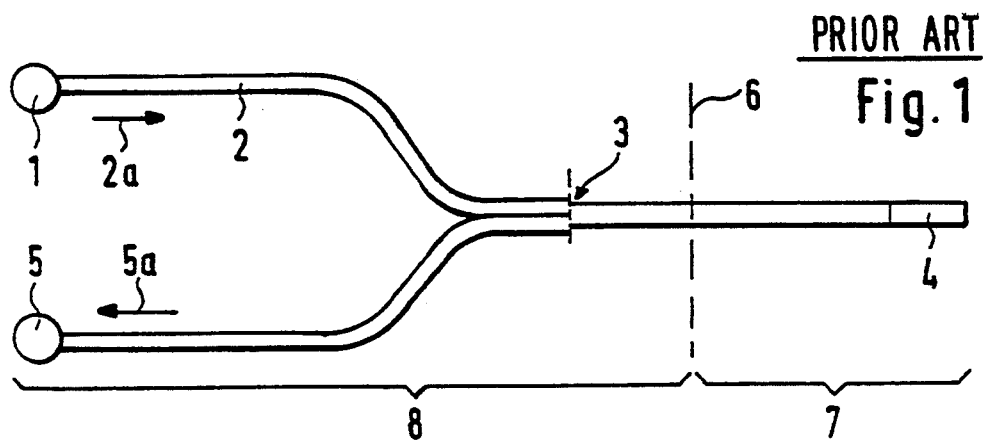
FIG. 1 depicts the basic operating principle of a prior art optical system for the invasive measurement of blood parameters.

It has now been found that the reading errors occurring after mechanical stress are caused by a specific mechanical problem. The glue used to fasten the sensor tips in the shield normally cannot be too hard. In fact, often a weak glue is used. This is because the glue has to be permeable to gas molecules. (A silicone glue fits these requirements.) However, in certain mechanical stress situations, the probe is subject to strong bending stress, e.g., caused by curvature of a blood vessel, or if a catheter is used for insertion of the probe into a blood vessel. In these cases, bending forces are transmitted by the optical fibers, insofar as they are located outside the sheath, to the parts of the sensors inside the sheath and, due to the weakness of the glue, this causes movement of the parts of the optical fibers inside the sheath relative to the dye-containing gel. Therefore, only part of the light transmitted by the fiber passes through the gel, and this, in turn, affects the accuracy of the sensor. Even worse, in many cases, the glue is not purely elastic, but has also plastic or viscous properties. As such, the optical fiber in the sheath does not completely return to its original position when the bending stress ends. That is, the stress causes a permanent reduction of measurement accuracy.

Further, the movement of the parts of the optical fiber extending into the sheath during bending stress causes a displacement of the dye-containing gel. When the bending stress ends, the gel does not return to its original position, thus further impairing accuracy. This happens even if the glue is purely elastic, i.e., if the optical fiber completely returns to its original position; however, in most cases both effects can be observed, and neither the optical fiber nor the gel return to their original position.

The present invention solves this problem in that the sheath is deformed with respect to its originally circular shape at least in the region adjoining the tube such that the circumferential arcing angle of the sheath (the looping angle) in relation to at least one of the sensors is larger than in the case of circular cross-section. In other words, the radius of curvature of the sheath, in the region next to or adjoining the sensor, is smaller than in the circular case.

It has been found that movement of the portions of the optical fibers extending into the sheath can be avoided, even if a relatively weak glue is used, if the optical fibers have a better mechanical fixing or contact to the sheath in the region where they enter the sheath (that is, the region of the sheath adjoining the tube). This is achieved in that the looping angle of circumference of at least one of the sensors is made larger than in the original circular configuration. Such "deformation" of the sheath may, be obtained by crimping the sheath, as will be explained. By means of the increased looping angle of circumference, the respective optical fiber is in better mechanical contact to the sheath, which in turn prevents it from moving inside the sheath.

Surprisingly, it has been found that such crimping in the region of the sheath adjoining the tube is even sufficient to avoid or restrict movement of the proximal end of the optical fiber inside the sheath; no further measure required. In particular, it is not necessary to deform the sheath along its whole length or along the region covering the optical fibers. Although such embodiments are also covered by the present invention, they are not strictly required.

In an alternative embodiment of the present invention, the sheath is deformed with respect to its originally circular shape at least in the region adjoining the tube such that the area of the cross-section not occupied by the sensors is smaller than in the case of circular cross-section. This reduces the free-space sectional area, which in turn reduces the freedom of movement of the optical fibers, so that they are kept in their position relative to the dye-containing gel. The advantage of this design can also be obtained if the optical probe comprises only one sensor.

According to a manufacturing method provided by the present invention, the optical probe is mechanically assembled. In particular, the tube containing the optical fibers is preferably introduced into the sheath of originally circular shape. Then, the portion of the sheath adjoining the tube is mechanically deformed, preferably by crimping. Preferably, the deformed region is at least as long as the portion of the tube introduced into the sheath. The tube is then deformed as well, which results in additional stability (although it is not necessarily required that the tube extend into the sheath). According to a further advantageous step in the manufacturing method, a glue is either introduced into the sheath, or is applied to the outside of the tube, before these two components are assembled. Deformation is then performed before the glue has hardened. This provides a further increase in stability. It is understood that the glue used for the fixing of the tube inside the sheath need not necessarily be the same as the glue used for fixing the sensors inside the sheath; on the contrary, as the glue near the distal end of the sheath need not be permeable to gas molecules, a glue of harder consistency may advantageously be used (thus further increasing mechanical stability).

Figure 4:
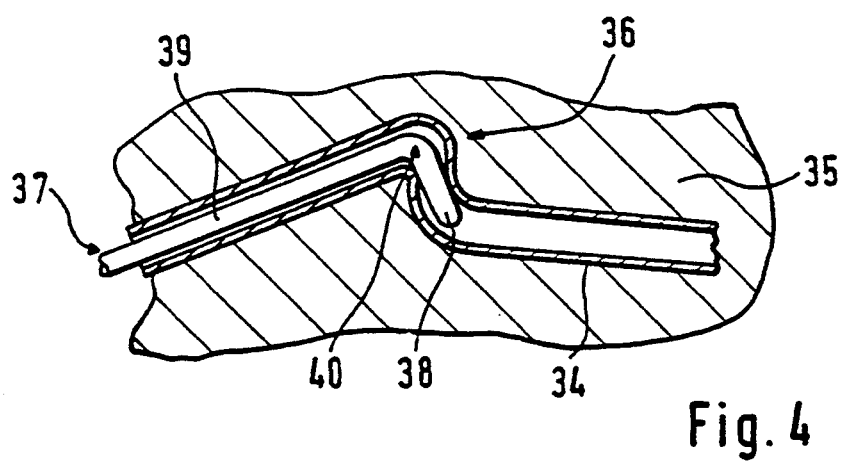
FIG. 4 depicts the mechanical problem encountered when an optical probe of the prior art is introduced into a curved vessel or catheter.

When introduced into a blood vessel, the optical probe is subject to mechanical bending stress. This is illustrated (in an exaggerated manner) in FIG. 4. Blood vessel 34 (e.g., an artery) of a patient—whose surrounding tissue is labeled as 35—has a strong curvature 36. Optical probe 37 is introduced into such a blood vessel. Due to the hard consistency of metal sheath 38, which cannot be bent, all of the bending stress is exerted on the transition between sheath 38 and tube 39 (the region labeled 40).

Figure 2:
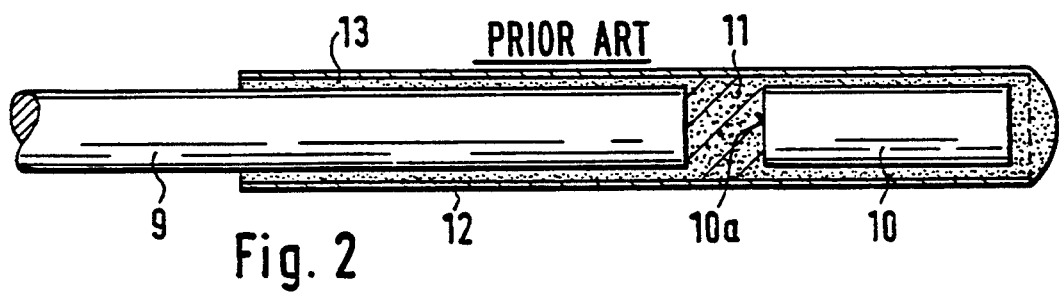
FIG. 2 is a longitudinal section of a single blood parameter sensor for incorporation into a prior art optical probe.

FIG. 5 depicts, in a drawing similar to that of FIG. 2 and with the same references numbers, what happens inside the sensors when such bending stress occurs at the transitional point between sheath and tube. This figure is also somewhat exaggerated in order to clearly show the resulting effects.

If the optical fiber 9 is subjected to bending stress, as indicated by arrow 41, the bending forces are transmitted to the internal part 9' of the fiber 9 (the part extending into the sheath). This internal part 9' of the fiber 9 is then squeezed towards membrane 12 (see arrow 42). Internal part 9' of the optical fiber 9 is displaced with respect to the dye-containing gel 11, and the optical axes of fiber 9, internal part 9', and reflector 10 are no longer aligned. Further, gel 11 is also displaced (according to FIG. 5, in the upward direction). This results in a deviation of the indicated pH (or $pO_2$, or $pCO_2$) value (reduced accuracy of the sensor).

Such deviation of the sensor reading is not limited to situations where the probe is subject to bending stress. The deviation does not disappear if the sensor is released from bending stress. The resulting effects are illustrated in FIGS. 6a and 6b, which depict the sensor of FIG. 5 when the bending stress has ended (i.e., because the probe has been pushed further into the blood vessel, or in that it has been withdrawn). FIG. 6a illustrates that the internal part 9' of the optical fiber 9 does not completely return to its original position. Likewise, FIG. 6b illustrates an environment where the optical fiber 9 has returned to its original position, but the gel 11' remains displaced. In both cases, the deviation of the sensor reading becomes permanent, or the accuracy of the sensor has been permanently impaired. (In most applications, the effects of both FIGS. 6a and 6b can be observed).

Figure 3:
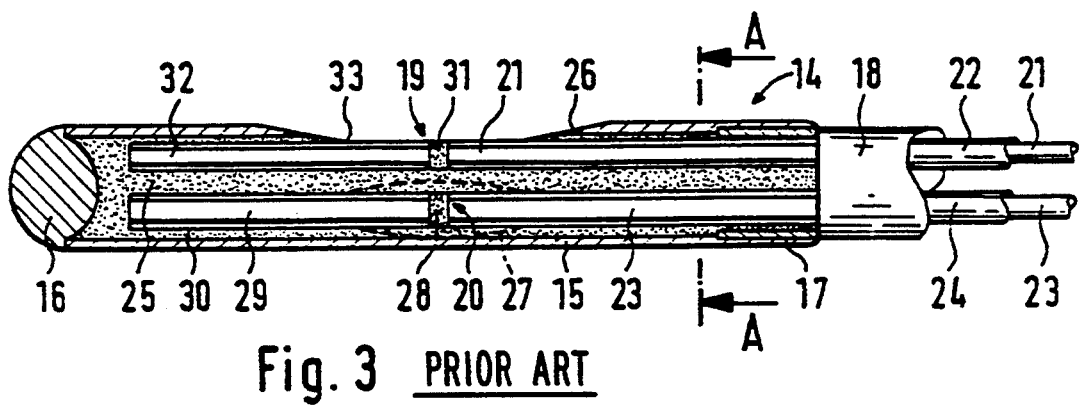
FIG. 3 is a longitudinal section of a prior art optical probe comprising a multiplicity of blood parameter sensors.

FIG. 7 depicts a cross-section of the prior art probe of FIG. 3 taken along line A—A of FIG. 3 (with the exception that FIG. 7 additionally shows a strain relieving wire 44). Sheath 15 surrounds pH sensor 19, $pCO_2$ sensor 20, $pO_2$ sensor 43, and a strain relieving wire 44 (not depicted in FIG. 3). The cross-section further depicts the optical fibers 21, 23, and 45 of the sensors, their surrounding selective membranes 33, 30, and 46, and glue 25.

In accordance with the invention, the sheath 15 of the type as shown in FIG. 7 is deformed from its originally circular-shaped cross-section in the region adjoining the tube such that the mechanical coupling between sheath and fibers is improved, or, in other words, that the sheath absorbs the bending forces exerted on the tube and the optical fibers. This can, e.g., be performed by crimping the sheath in the related region.

There are several possibilities for increasing the looping angle of circumference or reducing the free-space sectional area. However, tests have shown that a polygon-like contour yields excellent results. In particular, a rectangular (in the case of 4 sensing means) or triangular (in the case of 3 sensings means) shape not only improves the accuracy considerably, but also these shapes are easy to manufacture. Rounded edges of such polygon-like shapes reduce the danger of injury to the blood vessels. Nevertheless, there are further advantageous shapes like an ellipsoid, a cloverleaf-like shape, etc. that are contemplated by the present invention.

According to one aspect of the invention, the sheath of the optical probe has, at least in the region adjoining the tube, a cross-section that deviates from the circular shade such that the looping angle of circumference of the sheath in relationg to at least one of the sensors is larger than in the case of circular cross-section. According to another advantageous embodiment, the sheath has, at least in the region adjoining the tube, a cross-section wherein the area of the cross-section not occupied by the sensors is smaller than in the case of circular cross-section.

Figure 8:
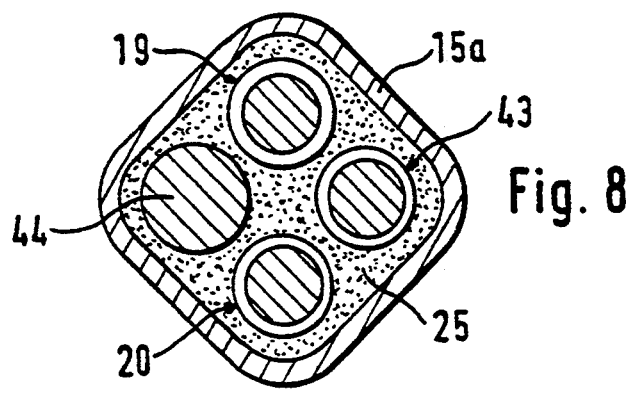
FIG. 8 is a cross-section, along line B—B of FIG. 12, of one embodiment of an optical probe according to the present invention.
Figure 12:
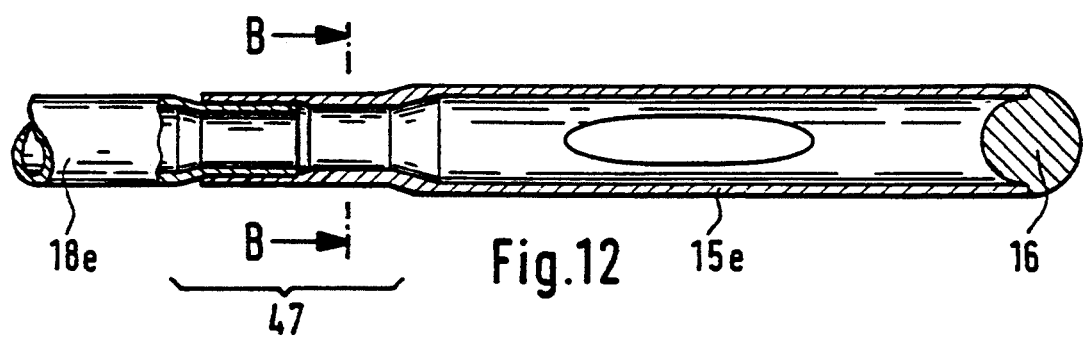
FIG. 12 is a longitudinal section of an optical probe according to the present invention.

FIG. 8 depicts an example of the probe after deformation of the sheath 15 in accordance with the present invention (cross-section along line B—B of FIG. 12). In this case, the circular sheath 15 has been deformed to a rectangular shape. The result is that the looping angle of circumference of the sheath, with respect to all sensors 19. 20, and 43, is increased, compared to the circular configuration. Its radius of curvature has become smaller. This increases stability and form-locking in the critical region. Likewise, the free-space sectional area is decreased.

Figure 9:
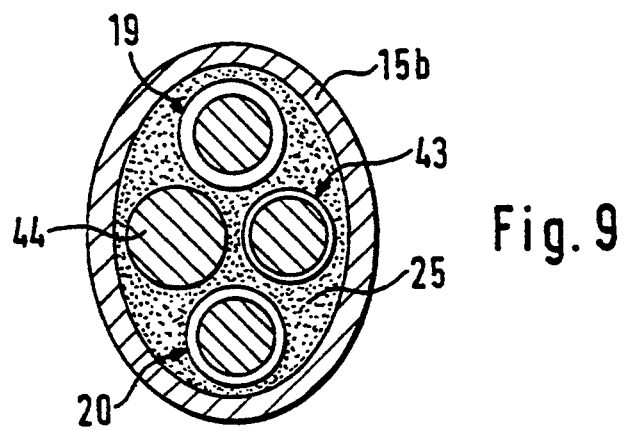
FIG. 9 is a cross-section, along line B—B of FIG. 12, of a second embodiment of an optical probe according to the present invention.

Another embodiment showing an alternate deformation is shown in FIG. 9. In this example, the cross-sectional shape of sheath 15b has been deformed to an ellipse. This also decreases the free-space sectional area and increases the looping angle of circumference around pH sensor 19 and $pCO_2$ sensor 20. Although the looping angle of circumference around wire 44 and $pO_2$ sensor 43 is not increased, the shown embodiment still ensures considerable reduction of measurement errors and is particularly easy to manufacture.

Figure 10:
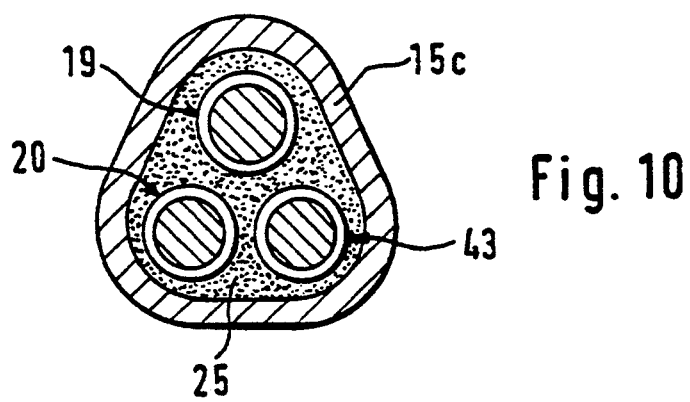
FIG. 10 is a cross-section, along line B—B of FIG. 12, of a third embodiment of an optical probe according to the present invention.

The examples of FIGS. 8 and 9 relate to an optical probe with 4 sensing means. However, the basic approach of the invention may also easily be applied to a probe with more or fewer sensing means. For example, FIG. 10 depicts an optical probe with three sensors 19, 20, and 43 but no strain-relieving wire, where sheath 15c has been deformed to a triangular shape. For an environment with 2 sensing means, one would, e.g., select an elliptic shape or a rectangular shape with two half-circles adjoining opposite edges of the rectangle.

Likewise, in case of 5 or more sensing means, a polygon-like shape can be used, preferably with rounded corners (the design with rounded corners is easier to manufacture and reduces the danger of injury of the patient's vascular wall).

Figure 11:
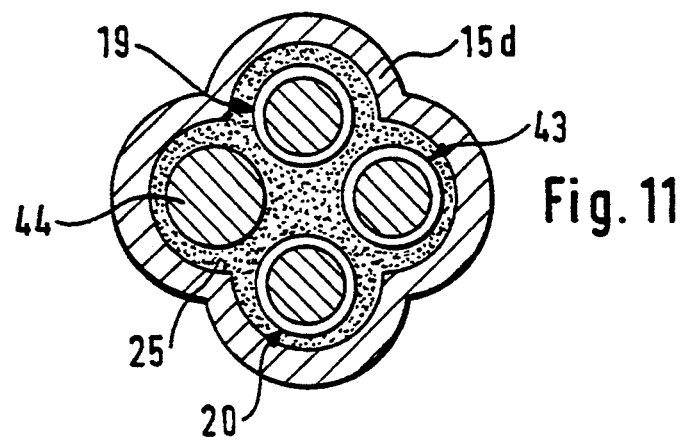
FIG. 11 is a cross-section, along line B—B of FIG. 12, of a fourth embodiment of an optical probe according to the present invention.

Another embodiment of the present invention, again with 3 sensors 19, 20, and 43 and a wire 44, is depicted in FIG. 11. Sheath 15d has been deformed to cloverleaf-like shape. This guarantees very good mechanical stability against bending forces; however, the shape of FIG. 11 is typically more difficult to manufacture than the shape depicted in FIGS. 8 to 10.

A longitudinal section of a crimped optical probe is depicted in FIG. 12. The deformed sheath is labeled as 15e and the deformed tube as 18e. For graphic purposes, the sensors have not been drawn in FIG. 12. The deformation of the sheath by crimping has been performed in the region labeled 47. FIG. 12 clearly shows that not only sheath 15e has been deformed, but also tube 18e extending into the sheath (this is not recognizable in FIGS. 8 to 11). This is an important feature of the present invention as the deformation of the sheath as well as the tube increases their mechanical coupling, thus avoiding the transmittal of bending forces to the proximal fiber ends inside the sheath. Upon manufacturing, a glue may further be applied to the distal inside of sheath 15e and/or the proximal outside of tube 18e, increasing stability further and preventing ions or gas molecules from reaching the inside of the sheath 15e. In this case, sheath and tube deformation are performed before the glue has hardened, thus avoiding cracks or fissures in the hardened glue. However, it is also possible to connect the tube and the sheath, and to deform the same, without additional glue.

In the embodiment of FIG. 12, the probe has been crimped along region 47 which is the most important region to avoid accuracy problems. However, it is understood that the present invention also relates to a smaller or a larger crimping region, even if it should extend along the complete sheath 15e.

Figure 13:
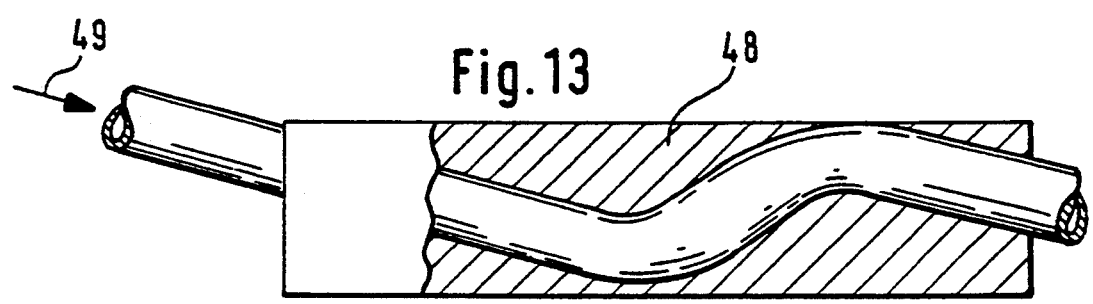
FIG. 13 depicts an artificial environment used to test the effect of bending stress on prior art probes and probes according to the present invention.

Tests have been made to verify the improved accuracy that can be obtained with the present invention. FIG. 13 depicts an artificial vessel (or catheter) 48 into which optical probes were introduced in the direction of arrow 49. The bending radius was selected such that introduction of the probe was still possible.

In the case of prior art (uncrimped) pH sensors, the tests revealed an average deviation between the original reading and the reading after insertion and withdrawal of $\Delta pH=0.022$. In the case of crimped pH sensors, this deviation was reduced to $\Delta pH=0.008$ on an average. Likewise, uncrimped $pCO_2$ sensors revealed an average deviation of $\Delta pCO_2=2.1$ Torr (279 Pa), whereas crimped $pCO_2$ sensors revealed $\Delta pCO_2=0.8$ Torr (106 Pa). That is, the invention reduced the signal deviation by a factor of approx. 2.6–2.7.

Figure 14:
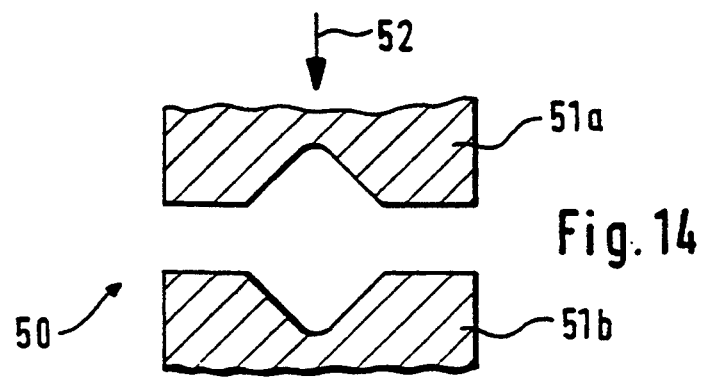
FIG. 14 is a cross-section of a first crimping tool.

FIG. 14 depicts the schematics of a tool 50 used to deform a probe with 4 sensing means. The circular-shaped probe is introduced between the two crimping elements 51a and 51b, and the upper element 51a is then moved in the direction of arrow 52 (alternatively, element 51b or both elements could be moved). This results in a deformation of the sheath to rectangular shape; however, only two edges of the sheath are rounded. To obtain a deformation with all edges rounded, it is necessary thereafter to turn the probe 90° and then to crimp it again.

Figure 15:
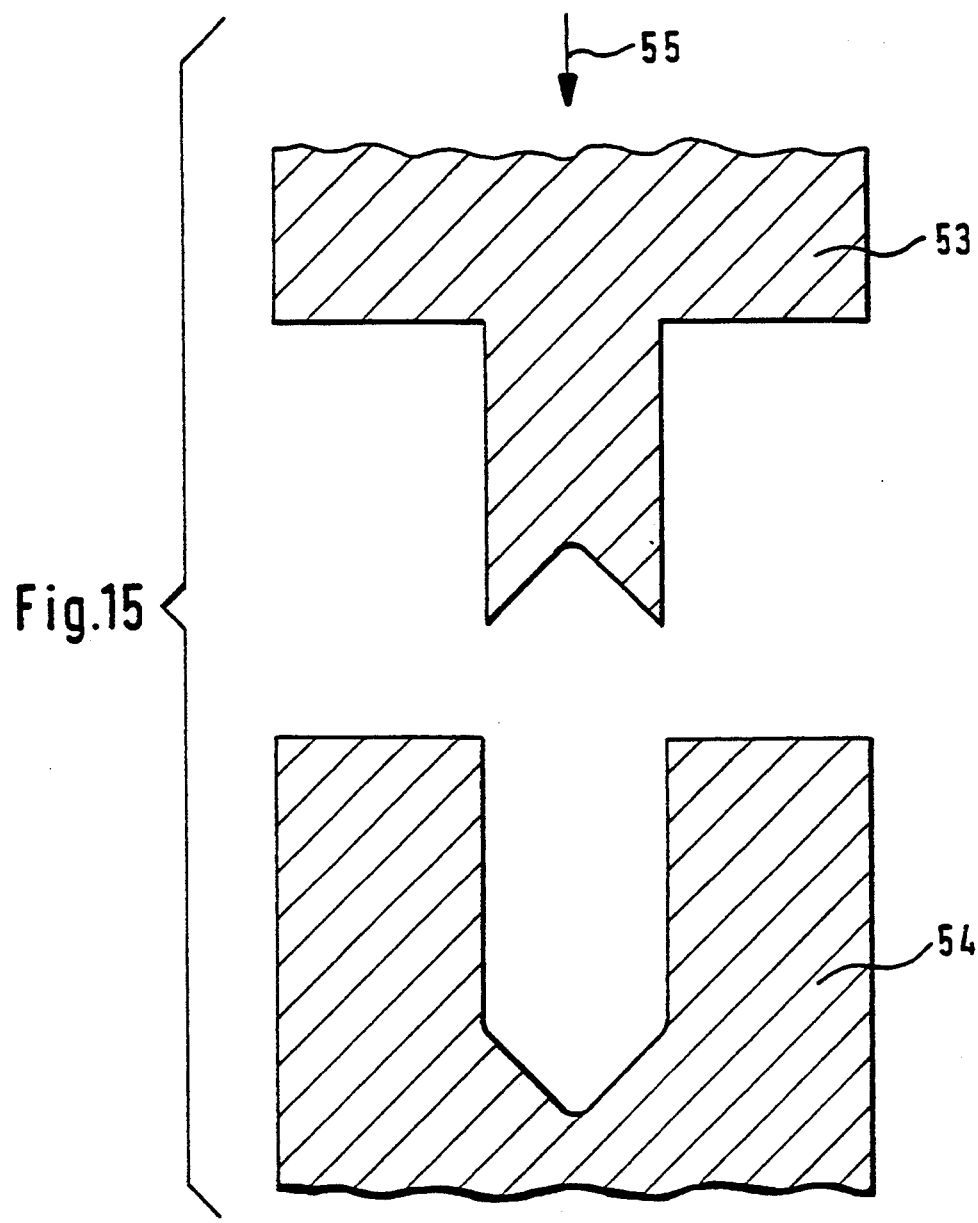
FIG. 15 is a cross-section of a second crimping tool.

In contrast, the crimping tool of FIG. 15 (elements 53 and 54) requires only one pass if element 53 is moved in the direction of arrow 55. In such a version, all edges are rounded after that pass.

Thus, an improved optical probe for the invasive measurement of blood gas parameters is disclosed. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A method for manufacturing an optical probe for the invasive measurement of blood parameters in a biologic circulatory system comprising the steps of:
   assembling an optical probe comprising a diffusion zone with a dye-containing gel that is optically sensitive to blood parameters, one or more sensing means having an end optically connected to said gel, a tube having an outside and an inside enclosing said sensing means except at said end, and a sheath having an outside and an inside enclosing said end and said gel and in contact with a portion of said tube, said sheath having a looping angle of circumference in relation to each of said sensing means;
   deforming said sheath with respect to its original cross-section at least in a region wherein said sheath contacts said tube such that the looping angle of circumference of the sheath in relation to at least one of said sensing means is increased.

2. The method of claim 1 wherein the step of deforming the sheath is accomplished by use of a crimping tool.

3. The method of claim 1 wherein said probe includes four sensing means and the deforming step deforms the sheath, at least in said region, into a substantially rectangular cross-section.

4. The method of claim 1 wherein said probe includes three sensing means and the deforming step deforms the sheath, at least in said region, into a substantially triangular cross-section.

5. The method of claim 1 wherein the deforming step deforms the sheath, at least in said region, into a substantially polygonal cross-section having rounded corners.

6. The method of claim 1 wherein a portion of the tube is designed to be inserted into said sheath and further comprising the steps of:
   applying a glue to the outside of said tube or to the inside of said sheath prior to inserting said tube into said sheath; and
   deforming said sheath before said glue has hardened.

7. A method for manufacturing an optical probe for the invasive measurement of blood parameters in a biologic circulatory system comprising the steps of:
   assembling an optical probe comprising a diffusion zone with a dye-containing gel that is optically sensitive to blood parameters, one or more sensing means having an end optically connected to said gel, a tube having an outside and an inside enclosing said sensing means except at said end, and a sheath having a side wall defining an outside and an inside and a cross section perpendicular to said side wall defining an area, said sheath enclosing said end and said gel and in contact with a portion of said tube;
   deforming said sheath with respect to its original cross section at least in a region wherein said sheath contacts said tube such that the area of the cross section of the sheath not occupied by said sensing means is smaller than in said original cross section.

8. The method of claim 7 wherein the step of deforming the sheath is accomplished by use of a crimping tool.

9. The method of claim 7 wherein said probe includes four sensing means and the deforming step deforms the sheath, at least in said region, into a substantially rectangular cross-section.

10. The method of claim 7 wherein said probe includes three sensing means and the deforming step deforms the sheath, at least in said region, into a substantially triangular cross-section.

11. The method of claim 7 wherein the deforming step deforms the sheath, at least in said region, into a substantially polygonal cross-section having rounded corners.

12. The method of claim 7 wherein a portion of the tube is desinged to be inserted into said sheath and further comprising the steps of:
   applying a glue to the outside of said tube or to the inside of said sheath prior to inserting said tube into said sheath; and
   deforming said sheath before said glue has hardened.

* * * * *